(12) United States Patent
Nagata et al.

(10) Patent No.: US 10,603,241 B2
(45) Date of Patent: Mar. 31, 2020

(54) CONTROLLER FOR MOTION ASSISTING APPARATUS, MOTION ASSISTING APPARATUS, METHOD FOR CONTROLLING MOTION ASSISTING APPARATUS, AND RECORDING MEDIUM

(71) Applicant: KABUSHIKI KAISHA YASKAWA DENKI, Kitakyushu-shi (JP)

(72) Inventors: Hideo Nagata, Kitakyushu (JP); Akira Yoshida, Kitakyushu (JP); Yuko Ikeda, Kitakyushu (JP); Yoshie Nakanishi, Kitakyushu (JP); Yoshie Murayama, Kitakyushu (JP)

(73) Assignee: KABUSHIKI KAISHA YASKAWA DENKI, Kitakyushu-Shi (JP)

( * ) Notice: Subject to any disclaimer, the term of this patent is extended or adjusted under 35 U.S.C. 154(b) by 328 days.

(21) Appl. No.: 15/468,120

(22) Filed: Mar. 24, 2017

(65) Prior Publication Data
US 2017/0273853 A1 Sep. 28, 2017

(30) Foreign Application Priority Data
Mar. 25, 2016 (JP) ................................ 2016-062513

(51) Int. Cl.
*A61H 3/00* (2006.01)
*A61B 5/103* (2006.01)
(Continued)

(52) U.S. Cl.
CPC ............ *A61H 3/00* (2013.01); *A61B 5/1038* (2013.01); *A61B 5/112* (2013.01); *A61B 5/1114* (2013.01);
(Continued)

(58) Field of Classification Search
CPC .............. A61H 3/00; A61H 2001/0211; A61H 1/0262; B25J 9/0006; B25J 9/16; A63B 22/02
See application file for complete search history.

(56) References Cited

U.S. PATENT DOCUMENTS

2006/0224246 A1* 10/2006 Clausen .................... A61F 2/66
 623/24
2006/0249315 A1* 11/2006 Herr .......................... A61F 2/60
 180/8.1
(Continued)

FOREIGN PATENT DOCUMENTS

CN 101917902 A 12/2010
CN 102176886 A 9/2011
(Continued)

OTHER PUBLICATIONS

Japanese Office Action for corresponding JP Application No. 2016-062513, dated Jan. 8, 2019 (w/ machine translation).
(Continued)

*Primary Examiner* — Bradley H Philips
*Assistant Examiner* — Vincent D Hoang
(74) *Attorney, Agent, or Firm* — Mori & Ward, LLP

(57) ABSTRACT

A controller for a motion assisting apparatus for a wearer includes circuitry. The circuitry is configured to set switching points in a change in a turning angle of a drive mechanism driven by a drive motor and attached to an ankle joint of the wearer to assist a turning motion of the ankle joint, a ratio of the change in the turning angle being equal to zero at the switching points. The circuitry is configured to set a motion pattern such that the turning angle monotonically increases or monotonically decreases between the switching points. The circuitry is configured to control the drive motor to change the turning angle according to the motion pattern.

19 Claims, 8 Drawing Sheets

(51) Int. Cl.
*A61B 5/11* (2006.01)
*A61B 5/00* (2006.01)
*A61H 1/02* (2006.01)
*A61B 5/107* (2006.01)

(52) U.S. Cl.
CPC .......... *A61B 5/1121* (2013.01); *A61B 5/4836* (2013.01); *A61B 5/6812* (2013.01); *A61B 5/6828* (2013.01); *A61B 5/6829* (2013.01); *A61H 1/0266* (2013.01); *A61B 5/1071* (2013.01); *A61B 5/1124* (2013.01); *A61B 5/6823* (2013.01); *A61B 2505/09* (2013.01); *A61B 2562/0219* (2013.01); *A61B 2562/0247* (2013.01); *A61H 2003/007* (2013.01); *A61H 2201/1207* (2013.01); *A61H 2201/164* (2013.01); *A61H 2201/165* (2013.01); *A61H 2201/1628* (2013.01); *A61H 2201/1676* (2013.01); *A61H 2201/5007* (2013.01); *A61H 2201/5028* (2013.01); *A61H 2201/5043* (2013.01); *A61H 2201/5061* (2013.01); *A61H 2201/5069* (2013.01); *A61H 2205/106* (2013.01)

(56) References Cited

U.S. PATENT DOCUMENTS

| | | | | |
|---|---|---|---|---|
| 2007/0123997 | A1* | 5/2007 | Herr | A61F 2/60 623/27 |
| 2010/0185301 | A1* | 7/2010 | Hansen | A61F 2/6607 623/47 |
| 2010/0271051 | A1 | 10/2010 | Sankai et al. | |
| 2011/0184225 | A1* | 7/2011 | Whitall | A63B 24/0003 600/28 |
| 2011/0205067 | A1 | 8/2011 | Konishi et al. | |
| 2012/0259429 | A1 | 10/2012 | Han et al. | |
| 2012/0259430 | A1* | 10/2012 | Han | A61F 2/60 623/24 |
| 2012/0289870 | A1* | 11/2012 | Hsiao-Wecksler | A61H 1/0266 601/5 |
| 2014/0200680 | A1* | 7/2014 | Holgate | A61F 2/60 623/24 |
| 2015/0081036 | A1* | 3/2015 | Nakanishi | A61H 1/024 623/24 |

FOREIGN PATENT DOCUMENTS

| | | |
|---|---|---|
| JP | 2005-000500 | 1/2005 |
| JP | 2009-213671 | 9/2009 |
| JP | 2014-226151 | 12/2014 |
| JP | 2015-058033 | 3/2015 |

OTHER PUBLICATIONS

Chinese Office Action for corresponding CN Application No. 201710187122, dated Apr. 15, 2019.

Japanese Office Action for corresponding JP Application No. 2016-062513, dated Oct. 31, 2019 (w/ machine translation).

Japanese Office Action for corresponding JP Application No. 2016-062513, dated Jul. 23, 2019 (w/ machine translation).

* cited by examiner

[FIG. 1]
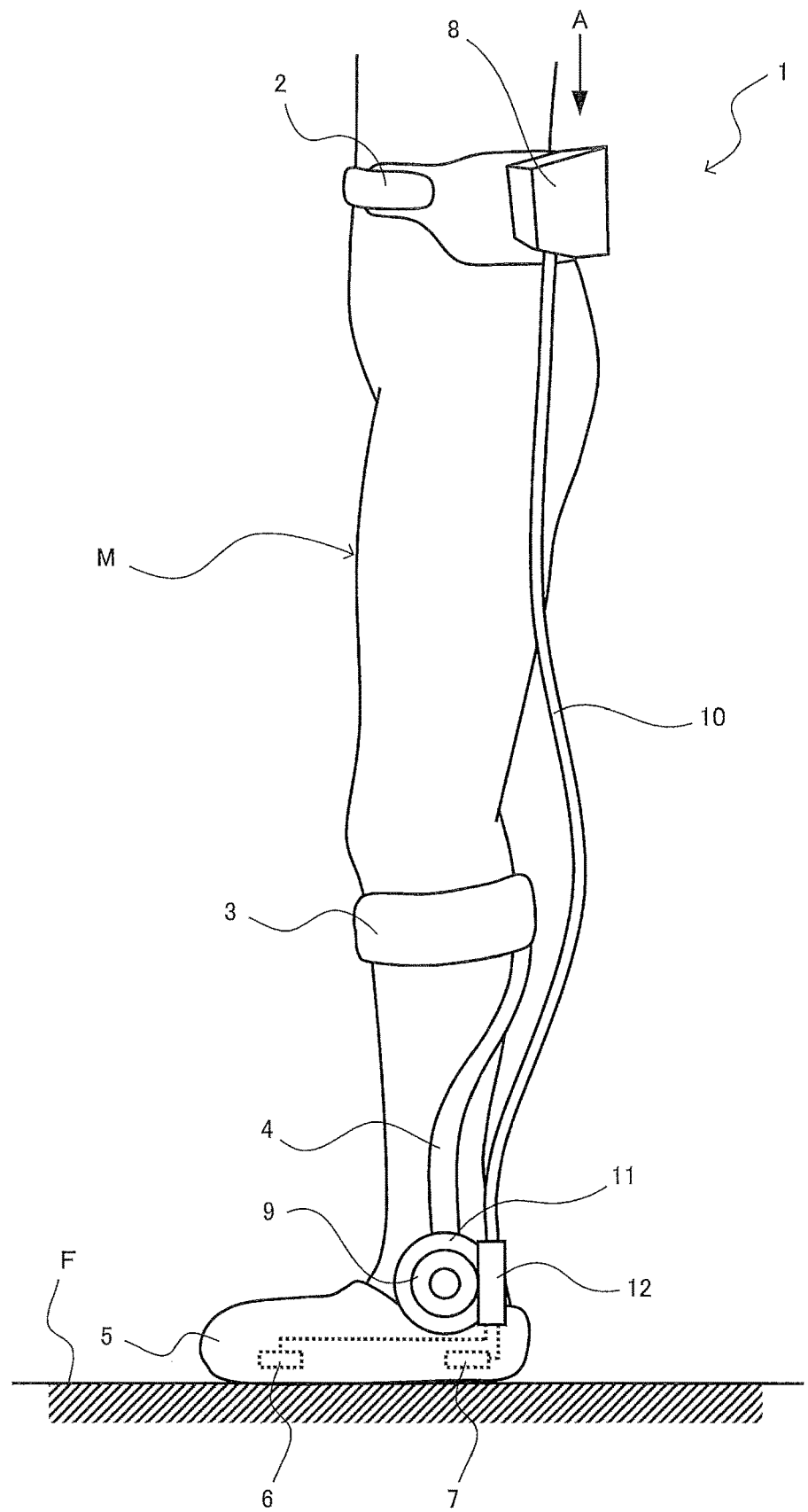

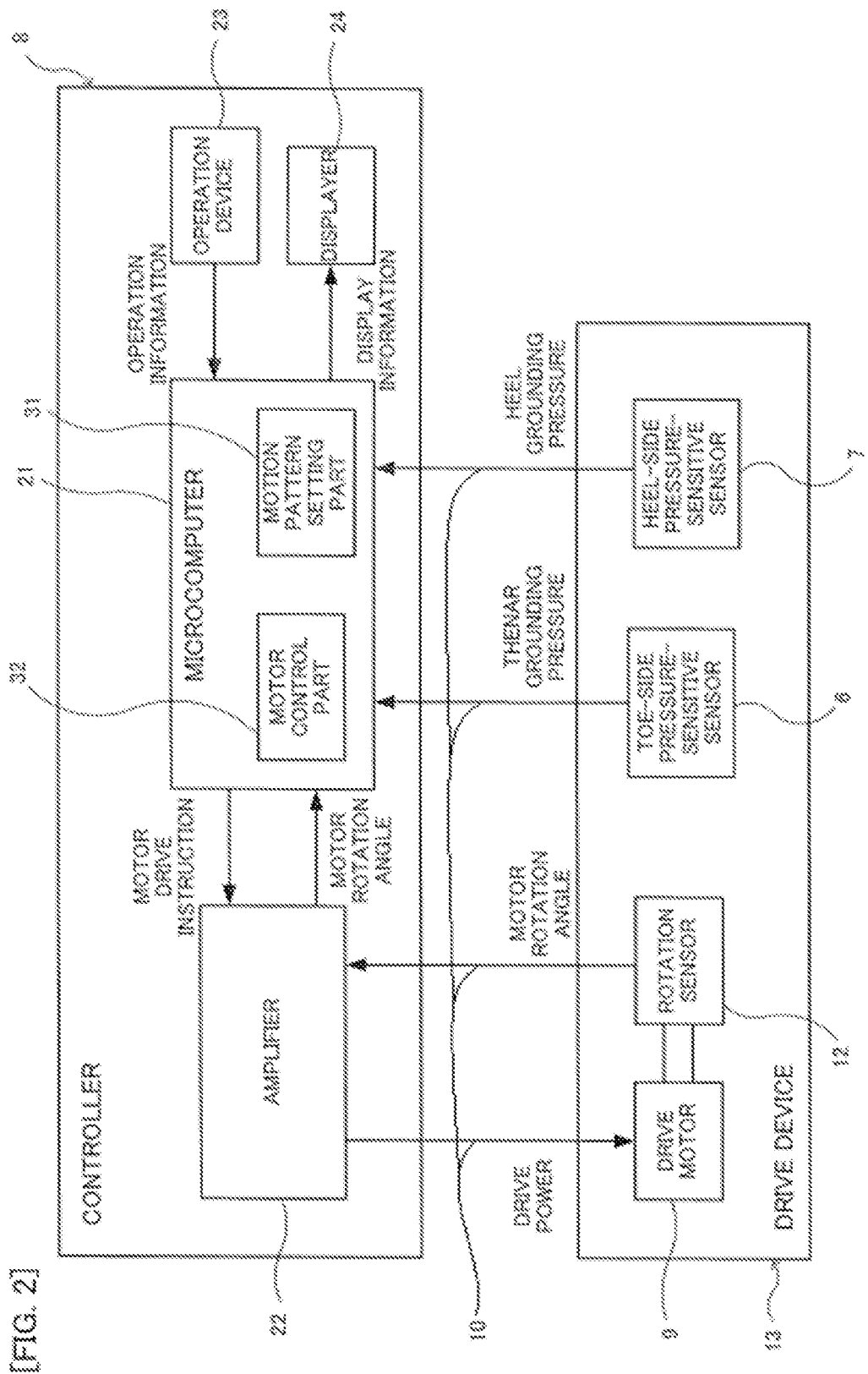
[FIG. 2]

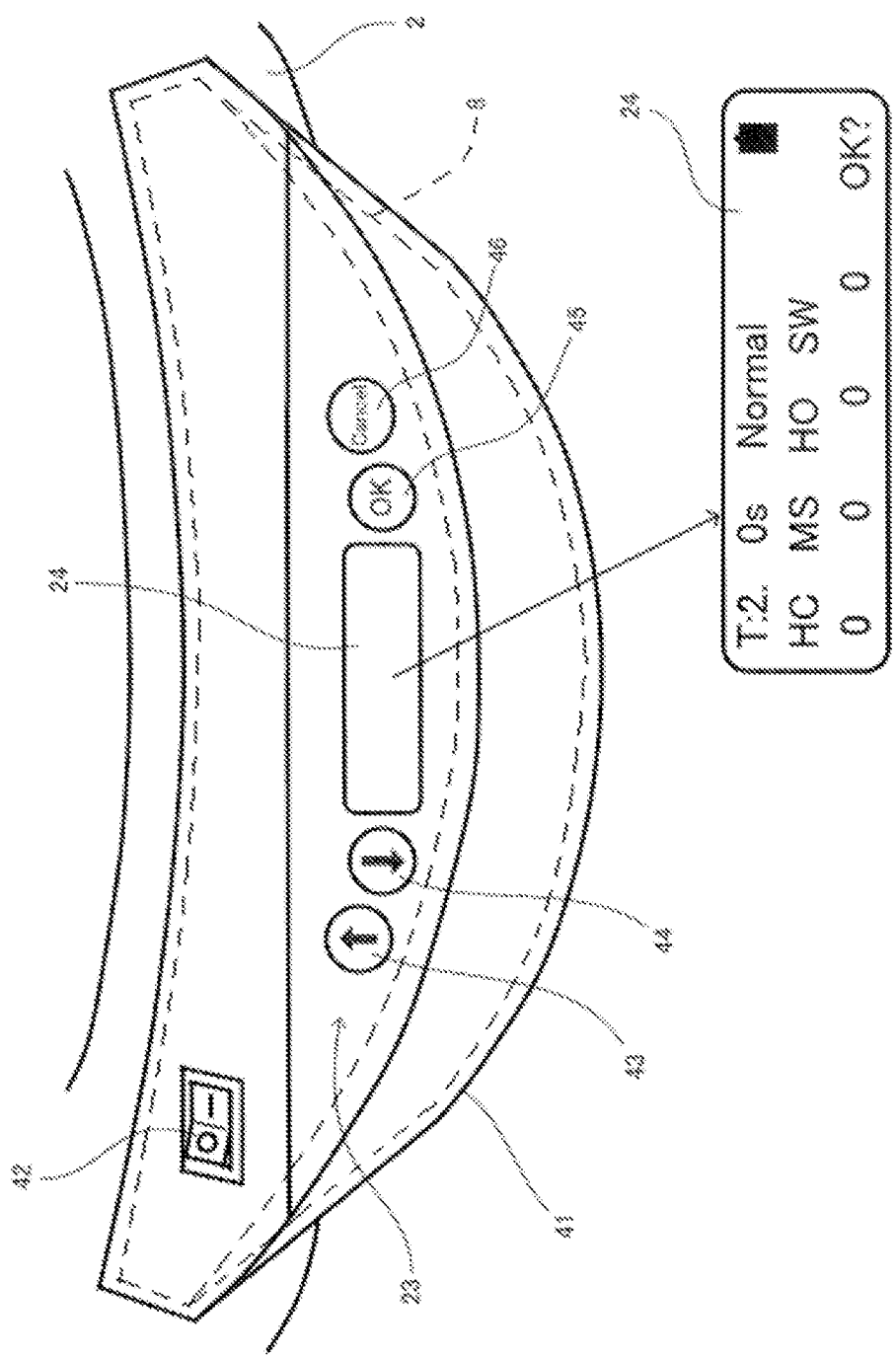
[FIG. 3]

[FIG. 4]
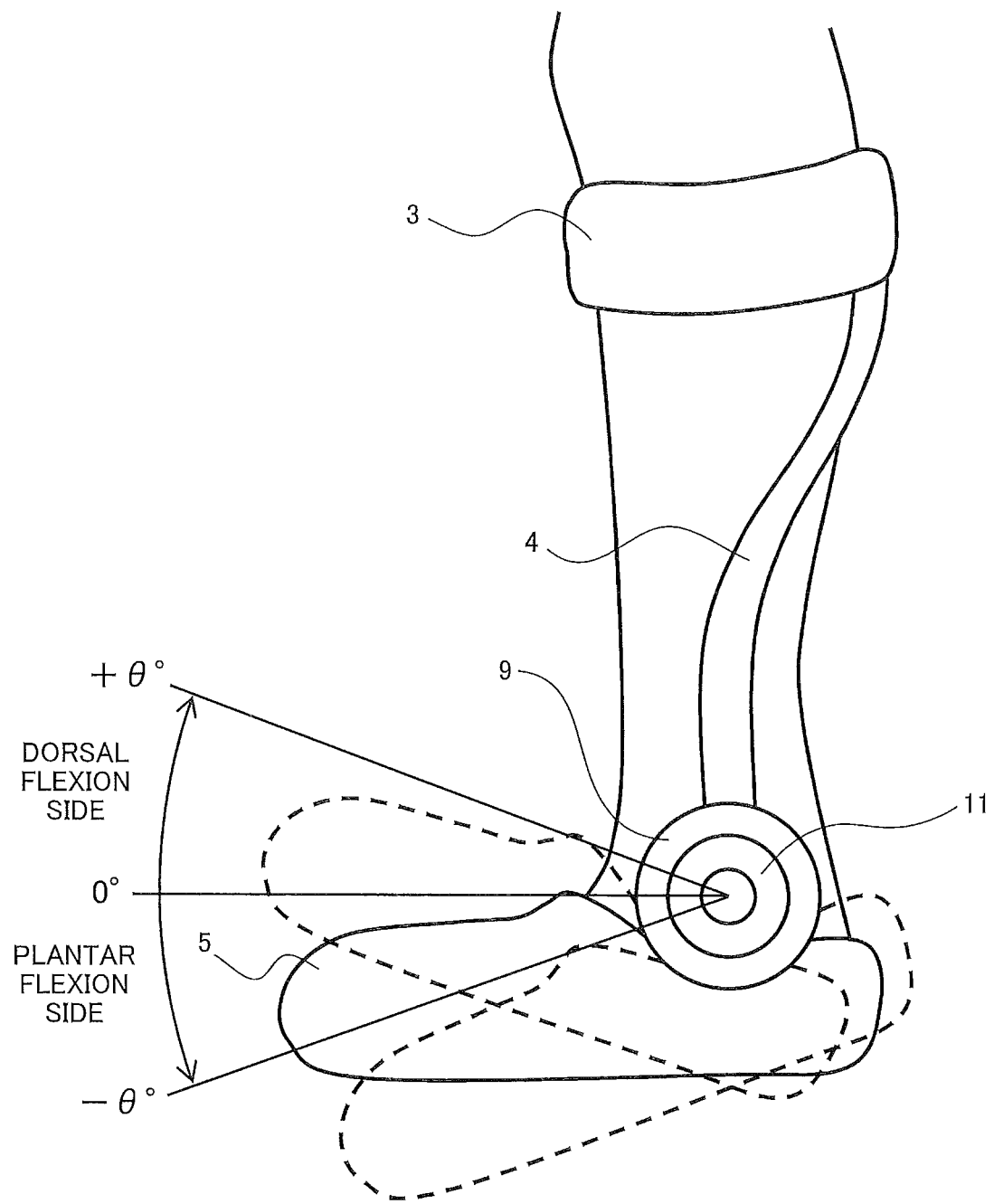

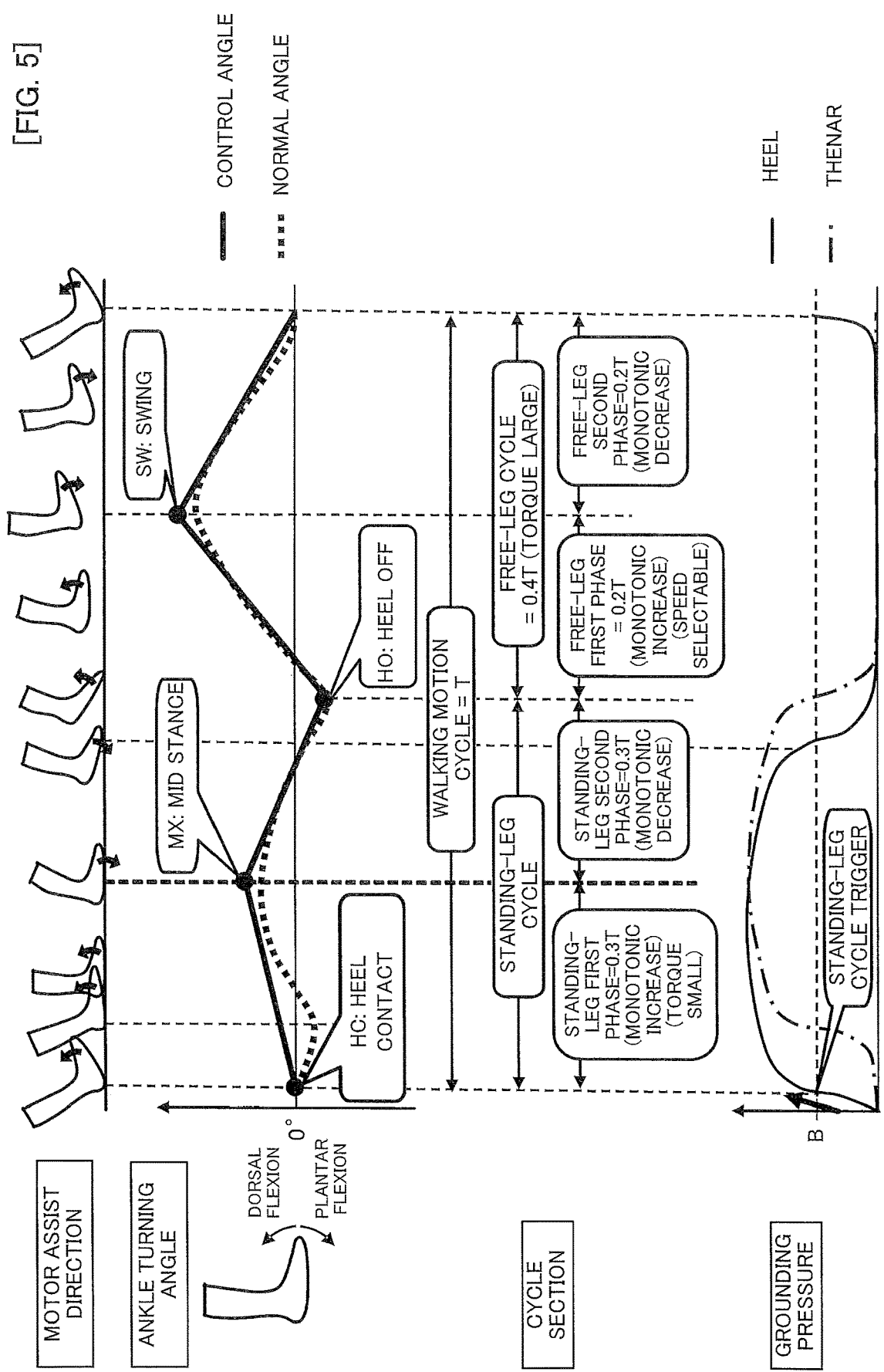

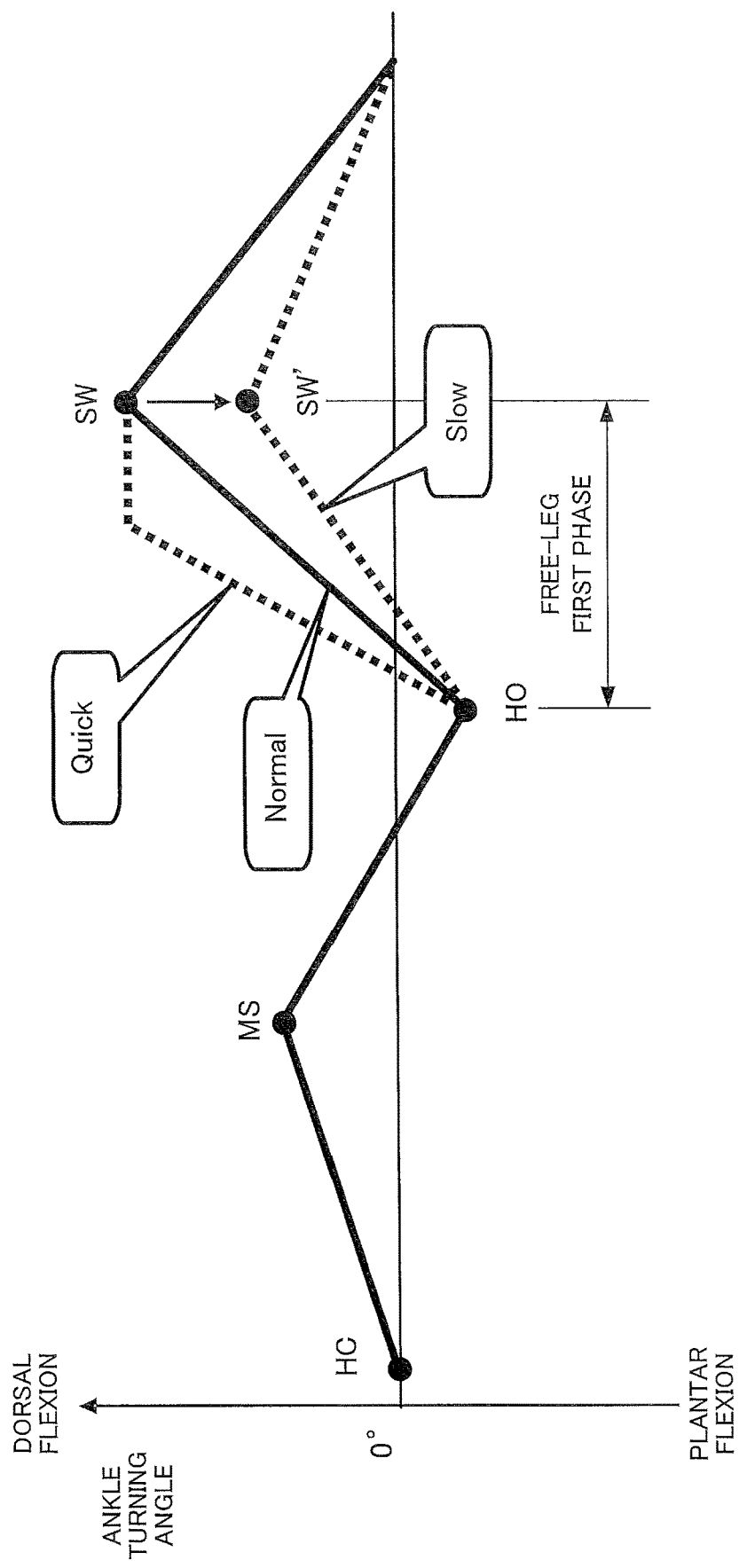
[FIG. 6]

[FIG. 7]
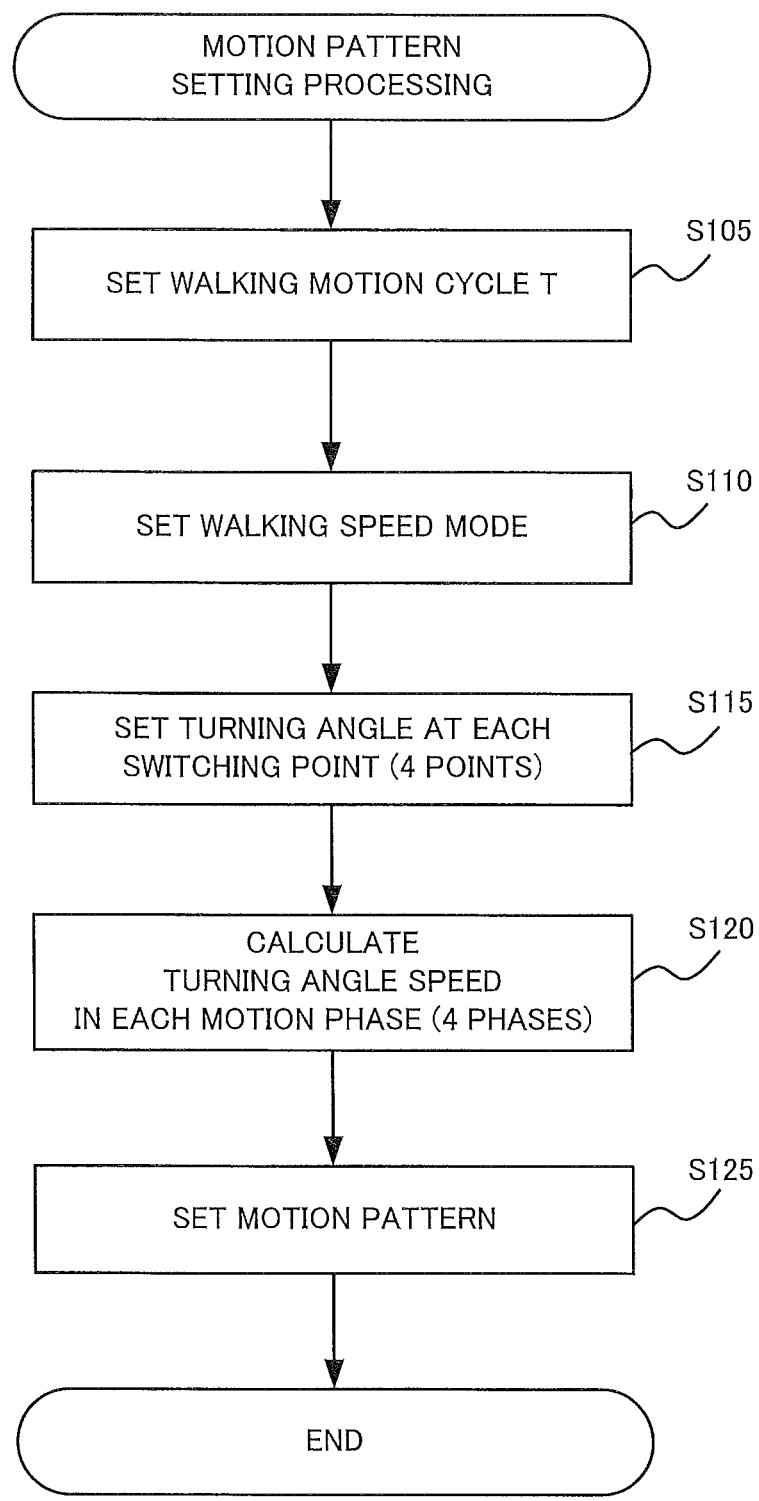

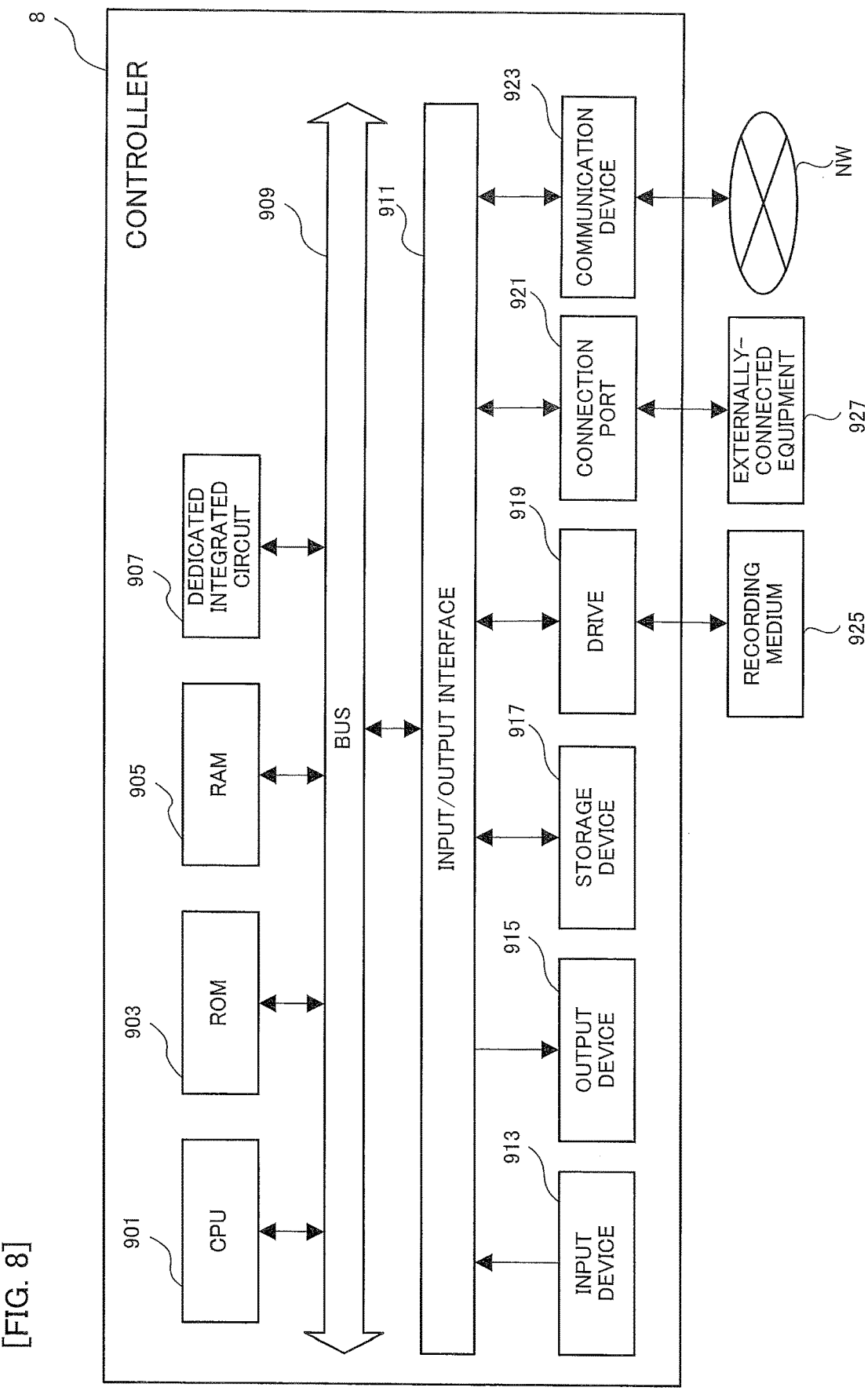
[FIG. 8]

CONTROLLER FOR MOTION ASSISTING APPARATUS, MOTION ASSISTING APPARATUS, METHOD FOR CONTROLLING MOTION ASSISTING APPARATUS, AND RECORDING MEDIUM

CROSS-REFERENCE TO RELATED APPLICATION

The present application is based upon and claims the benefit of priority to Japanese Patent Application No. 2016-062513, filed Mar. 25, 2016. The entire contents of this application are incorporated herein by reference.

BACKGROUND OF THE INVENTION

Field of the Invention

An embodiment of disclosure relates to a controller for a motion assisting apparatus, a motion assisting apparatus, a method for controlling a motion assisting apparatus, and a recording medium.

Description of Background Art

There is known a motion assisting apparatus which divides a motion pattern of a drive mechanism attached around a joint of a wearer at an equal time interval and sets the motion pattern by adjusting a motion state amount in each section.

SUMMARY OF THE INVENTION

According to one aspect of the present disclosure, a controller for a motion assisting apparatus for a wearer includes circuitry. The circuitry is configured to set switching points in a change in a turning angle of a drive mechanism driven by a drive motor and attached to an ankle joint of the wearer to assist a turning motion of the ankle joint, a ratio of the change in the turning angle being equal to zero at the switching points. The circuitry is configured to set a motion pattern such that the turning angle monotonically increases or monotonically decreases between the switching points. The circuitry is configured to control the drive motor to change the turning angle according to the motion pattern.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 is a side view of a waist part and a lower limb of a wearer wearing a motion assisting apparatus of an embodiment when seen from a left side;

FIG. 2 is a block configuration diagram conceptually illustrating an exemplary electric configuration of a control system of the motion assisting apparatus;

FIG. 3 is an enlarged appearance view of a controller when seen from an arrow view A in FIG. 1;

FIG. 4 is an enlarged view of a vicinity of a drive mechanism in FIG. 1;

FIG. 5 is a diagram for explaining an exemplary setting contents of a motion pattern;

FIG. 6 is a diagram for explaining an exemplary selection setting of a walking speed mode;

FIG. 7 is an exemplary flowchart illustrating a control procedure executed by a CPU of a microcomputer in order to realize motion pattern setting processing of the embodiment;

FIG. 8 is a block diagram illustrating an exemplary hardware configuration of the controller.

DETAILED DESCRIPTION OF THE EMBODIMENTS

An embodiment will be described below with reference to the attached drawings.

1. Entire Configuration of Motion Assisting Apparatus

FIG. 1 is a side view of a waist part and a lower limb of a wearer M wearing a motion assisting apparatus of an embodiment when seen from a left side. This motion assisting apparatus assists a turning motion of an ankle joint of the wearer M as an example. In FIG. 1, the motion assisting apparatus 1 has a waist-part brace 2, a shin-part brace 3, a shin-part arm 4, a shoe part 5, a toe-side pressure-sensitive sensor 6, a heel-side pressure-sensitive sensor 7, a controller 8, a drive motor 9, a cable 10, a drive mechanism 11, and a rotation sensor 12.

The waist-part brace 2 is a brace wound around a waist part of the wearer M. The waist-part brace 2 is stably attached to a position of the waist part of the wearer M where a waist circumference is the smallest.

The shin-part brace 3 is a brace wound around a shin part of the wearer M. The shin-part brace 3 is stably attached to a position immediately below a knee part in the illustrated example.

The shin-part arm 4 is a structure having a substantially beam shape. The shin-part arm 4 has its upper end fixed to the shin-part brace 3 and its lower end fixed to the drive mechanism 11 which will be described later.

The shoe part 5 is a shoe-shaped brace attached so that a foot of the wearer M is inserted therein. The shoe part 5 is stably attached so as to hold a posture of the foot. Further, a vicinity of an ankle of the shoe part 5 is also fixed to the drive mechanism 11 which will be described later. Here, entirety including the shin-part brace 3, the shin-part alai 4, and this shoe part 5 constitutes a so-called short leg brace. Note that the short leg brace may be constituted by fixing an insole made of a resin, for example, inserted into a shoe sole therein to the drive mechanism 11 instead of the shoe part 5. In this case, although not particularly shown, the insole is made a stirrup-shaped frame to be directly fixed to a periphery of the foot of the wearer M, and this stirrup-shaped frame with the foot wearing it may be inserted into the shoe part 5 to be worn.

The toe-side pressure-sensitive sensor 6 (an embodiment of a second detector) is a pressure sensor disposed so as to be brought into direct contact with a vicinity of a toe-side thenar of the wearer M on the shoe sole inside the shoe part 5. The toe-side pressure-sensitive sensor 6 detects a grounding pressure of the thenar of the wearer M against a floor surface F. The heel-side pressure-sensitive sensor 7 (an embodiment of a first detector) is a pressure sensor disposed so as to be brought into direct contact with a heel of the wearer M on the shoe sole inside the shoe part 5. The heel-side pressure-sensitive sensor 7 detects a grounding pressure of the heel of the wearer M against the floor surface F. Note that, in the case that the stirrup-shaped frame is disposed, the toe-side pressure-sensitive sensor 6 and the heel-side pressure-sensitive sensor 7 are disposed not on the shoe sole inside the shoe part 5 but on a bottom surface of the stirrup-shaped frame, and they only need to be arranged between the bottom surface of the stirrup-shaped frame and the shoe sole at the time of wearing (not shown).

As illustrated in FIG. 2 which will be described later, the controller 8 includes an amplifier 22, an operation device 23, a displayer 24, and a battery (not particularly shown) for feeding power to each part of the motion assisting apparatus 1. Further, the controller 8 has a motion pattern setting part 31 for setting a motion pattern which will be described later and a motor control part 32 for drive-controlling the drive motor 9 on the basis of this motion pattern as functional configuration. This controller 8 is fixed to a back surface of the waist-part brace 2 in the illustrated example, that is, it is arranged on a back surface of a waist part of the wearer M at the time of wearing the waist-part brace 2. The controller 8 supplies drive power to or transmits/receives an electric signal to/from the drive motor 9 and various sensors arranged in a periphery of a foot part of the wearer M through the flexible cable 10. Note that details of this controller 8 will be described later.

The drive mechanism 11 has a decelerator and a drive shaft, although not particularly shown. In this example, the decelerator is fixed to the lower end of the shin-part arm 4, and the drive shaft is fixed to a rear upper part of the shoe part 5 (or the stirrup-shaped frame). With this constitution, the entire drive mechanism 11 functions as a hinge rotationally movable coaxially with the ankle joint of the wearer M.

The drive motor 9 is a rotary motor rotating/driving an output shaft. Since the output shaft of the drive motor 9 is connected to an input shaft of the decelerator, a rotary driving force of the drive motor 9 is decelerated by the decelerator and increases a torque, which is output to the drive shaft. As a result, the shoe part 5 (or the stirrup-shaped frame) performs a relative turning motion around the drive shaft with respect to the shin-part arm 4 and the shin-part brace 3. Since a position of this drive shaft is arranged on a side of the ankle joint (ankle) of the wearer M substantially coaxially, the drive mechanism 11 can assist the turning motion of the ankle joint of the wearer M. Here, the decelerator may be fixed to the shoe part 5 (or the stirrup-shaped frame), and the drive shaft may be fixed to the shin-part arm 4. In this case, a direction of the relative turning motion is opposite, but it is possible to perform control by switching between forward rotation and backward rotation of the drive motor 9 oppositely.

The rotation sensor 12 is an encoder for detecting a rotation angle of the drive motor 9. The rotation sensor 12 is disposed so as to have a positional relationship to be orthogonal to the output shaft in order to reduce a side width dimension (axial length) of the drive motor 9 in the illustrated example.

2. Control Configuration of Motion Assisting Apparatus

FIG. 2 is a block configuration diagram conceptually illustrating an electric configuration of the control system of the motion assisting apparatus 1. In this FIG. 2, an element group of the drive motor 9, the rotation sensor 12, the toe-side pressure-sensitive sensor 6, and the heel-side pressure-sensitive sensor 7 arranged in a periphery of the shoe part 5 constitutes a drive device 13. The controller 8 and the drive device 13 transmit/receive drive power and various electric signals through the cable 10.

The controller 8 includes a microcomputer 21, the amplifier 22, the operation device 23, and the displayer 24. Drive power output by the amplifier 22 is fed to the drive motor 9 of the drive device 13 through the cable 10. Detection values of various sensors 6, 7, and 12 included in the drive device 13 are input into the controller 8 through the cable 10. The microcomputer 21 is a so-called computer including a CPU (arithmetic device included in the controller 8) which will be described later, a ROM, a RAM, and a non-volatile storage device such as a flash memory, and controls the entire motion assisting apparatus 1. Further, this microcomputer 21 has the motion pattern setting part 31 performing setting of a motion pattern which will be described later and the motor control part 32 performing drive control of the drive motor 9 on the basis of this motion pattern.

Note that processing and the like in the motion pattern setting part 31, the motor control part 32 and the like described above are not limited to the example of processing sharing described above but may be executed by fewer processing parts (one processing part, for example) or may be executed by further fragmented processing parts. Further, the motion pattern setting part 31, the motor control part 32 and the like may be implemented by a program executed by a CPU 901 (see FIG. 8) which will be described later or a part of or the whole of them may be implemented by an actual device such as ASIC, FPGA and other electric circuits.

The amplifier 22 feeds drive power to the drive motor 9 on the basis of a motor drive instruction input from the motor control part 32 of the microcomputer 21 and controls its driving. The drive motor 9 physically transmits its rotary driving force to the drive mechanism 11 as described above. The rotation sensor 12 disposed in the drive mechanism 11 detects the rotation angle (rotation position) of the drive motor 9 and transmits it to the amplifier 22. The amplifier 22 performs positional feedback control by a so-called semi-closed loop by using the detection value of this rotation sensor 12. Further, the amplifier 22 outputs the detection value of the motor rotation angle input from the rotation sensor 12 to the microcomputer 21.

The operation device 23 includes a power switch and receives various input operations and outputs input operation information to the microcomputer 21. The displayer 24 displays various types of display information such as setting parameters, internal states, and instructions input from the microcomputer 21.

3. Specific Configuration of Operation Device, Displayer

An exemplary specific configuration of the operation device 23 and the displayer 24 is illustrated in FIG. 3. FIG. 3 illustrates an appearance of the controller 8 when seen from an arrow view A in FIG. 1. The controller 8 is contained in a housing 41 having a substantially crescent shape in general, for example. On an upper surface of the housing 41, the operation device 23 and the displayer 24 are arranged. The operation device 23 has a power switch 42 and four push button keys 43, 44, 45, and 46. In the illustrated example, two of the four push button keys are cursor operation keys 43 and 44, one of them is an OK key 45, and the remaining one is a cancellation key 46. The displayer 24 is constituted by a liquid crystal display having a generally rectangular shape, for example. An operator (a caregiver which will be described later) operating the controller 8 performs switching of display contents on the displayer 24, selection of setting items in the display screen, setting of setting contents and the like by operating the two cursor operation keys 43 and 44 and performs operations of determining and stopping of the operation contents with the OK key 45 and the cancellation key 46. Note that an exemplary specific display and an exemplary operation will be described later in detail.

4. Motion Pattern Setting Processing

The motion assisting apparatus 1 constituted as above causes the drive mechanism 11 to perform a relative turning motion between the shoe part 5 and the shin-part arm 4 around the ankle joint using the drive motor 9 as a drive source.

The motion assisting apparatus 1 drives the drive mechanism 11 with a turning angle which corrects an active joint motion by the wearer M such as a paralytic to a normal motion as much as possible with the purpose of use in rehabilitation to the paralytic or the like. However, a temporal change pattern of a motion of the paralytic is greatly varied depending on a degree of a symptom or an individual difference. Thus, in the case that the motion assisting apparatus 1 is operated with a motion pattern not suitable for the paralytic, it undermines an effect of the rehabilitation to the contrary. Thus, the motion pattern of the drive mechanism 11 is preferably set in accordance with a situation of the wearer M, but a setting operation of such a motion pattern may become very cumbersome at a site of actual nursing. In the case of the motion assisting apparatus 1 applied particularly to an ankle joint, a change pattern of a turning angle of the ankle joint is complicated even in a normal walking motion cycle. Thus, it has been difficult to adjust and set a motion pattern of the motion assisting apparatus 1 in accordance with the situation of the wearer M.

On the other hand, it has been newly found that a motion pattern which is effective to be used for rehabilitation can be set only by time-dividing a motion pattern of a turning angle of the drive mechanism 11 during a walking motion cycle by the unit of a motion phase for monotonic increase or monotonic decrease and by setting the turning angle of the drive mechanism 11 at a switching point between those motion phases. In this embodiment, the motion pattern setting part 31 of the controller 8 sets and generates a motion pattern of the drive mechanism 11 in a simplified manner only by setting the turning angle at the switching points in a reduced number by this method, and the motor control part 32 controls driving of the drive motor 9 on the basis of the motion pattern. A process of the setting of the motion pattern as described above will be described in order below.

FIG. 4 illustrates a periphery of the drive mechanism 11 in FIG. 1 in an enlarged manner. Note that, in this FIG. 4, the rotation sensor 12 and the like are not shown. As illustrated by a solid line in this FIG. 4, a relative turning angle between the shoe part 5 and the shin-part arm 4 in a state where the wearer M normally stands up and a bottom surface of the shoe part 5 (back surface of a foot) is substantially orthogonal to a longitudinal direction of the shin part (a vertical direction in the figure) is assumed to be an initial angle of 0°. The rotation sensor 12 detects the turning angle obtained when a front tip end portion of the shoe part 5 is turned in a direction getting close to the shin part (upper side in the figure and hereinafter, referred to as a dorsal flexion side) as a positive value of 0. Moreover, the rotation sensor 12 detects the turning angle obtained when the front tip end portion of the shoe part 5 is turned in a direction separating away from the shin part (lower side in the figure and hereinafter, referred to as a plantar flexion side) as a negative value of 0.

Subsequently, an exemplary setting of a motion pattern will be described with reference to FIG. 5. In this FIG. 5, a lateral axis indicates elapse of time. Moreover, FIG. 5 illustrates an exemplary temporal change of a motor assist direction, an ankle turning angle, a cycle section, and a grounding pressure in order from above.

A time length in the entirety in a lateral direction (left-right direction) in the figure corresponds to a walking motion cycle T which is a unit cycle of a walking motion. This unit motion is cyclically repeated, and thus a consecutive walking motion is performed. Note that this walking motion cycle T uses a unit of a motion cycle paying attention only to a foot wearing the shoe part 5. Therefore, in a normal walking motion assuming that a motion only of stepping one of right and left feet forward is one step, a time length for "2 steps" corresponds to 1 cycle in the walking motion cycle T in this embodiment.

First, in the case of a normal walking motion performed by a healthy person, a foot moves in a state at each time point as illustrated in the illustration of the motor assist direction, and an ankle turning angle changes as illustrated by a dotted curve in the illustration of the ankle turning angle. That is, assuming that the foot is stepped to the front of an upper body of the wearer M and a time point when a heel is first grounded is made a starting point as illustrated on the leftmost side in the figure, the turning angle of the ankle at that time point is substantially 0°. Then, as the upper body of the wearer M moves forward, a toe is lowered, that is, the turning angle of the ankle is decreasingly changed to the plantar flexion side, and the entire back surface of the foot is grounded.

After that, the ankle turning angle increases to the dorsal flexion side exceeding 0° with movement of the upper body but after the entire leg portion extends to the rear to some degree, only the heel leaves the ground surface, and the ankle turning angle decreases to the plantar flexion side until lowering below 0°. Then, after the toe leaves the ground surface, the ankle turning angle increases to the dorsal flexion side exceeding 0° while the foot is made to swing forward. After that, when the foot is thrown out to the front of the upper body, the ankle turning angle decreases, and the ankle turning angle returns to substantially 0° at a time point when the heel is grounded.

A healthy person can unconsciously perform a changing motion of the ankle turning angle which forms a complicated temporal waveform (a normal angle indicated by a dotted curve in the figure) as above. However, in the case of a paralytic or the like, since the ankle turning angle is fixed to the same angle at all times, for example, it is likely that an inappropriate motion may occur such that the toe is grounded first instead of the heel which should have been grounded first. Originally, the turning angle at each time point should be finely adjusted in accordance with the symptom degree or an individual difference on the basis of the temporal waveform of the normal turning angle. However, in an actual nursing site, it is difficult for one caregiver to perform such cumbersome manual works many times while supporting the body of the wearer M.

Thus, in this embodiment, setting processing of the motion pattern of the drive mechanism 11 is performed by a method simplified as below. First, the walking motion cycle T is divided into a standing-leg cycle in a standing-leg state where at least a part of the foot is grounded on the ground surface and a free-leg cycle in a free-leg state where the entire foot is away from the ground surface. Then, in a first half of the standing-leg cycle, a motion period in which the foot grounded on the front of the upper body is withdrawn to the rear is referred to as a standing-leg first phase, while in a second half, a motion period in which the foot is kicked out to the rear of the upper body is referred to as a standing-leg second phase. Further, in a first half of the free-leg cycle, a motion period in which the foot located on the rear of the upper body is made to swing back to the front is referred to as a free-leg first phase, and a motion period in the second half in which the foot is made to swing forward to the front of the upper body is referred to as a free-leg second phase.

Then, the switching points between the aforementioned four motion phases are referred to as a heel contact point HC, a mid stance point MS, a heel off point HO, and a swing point SW, respectively. The heel contact point HC is a switching point when the free-leg second phase is switched to the standing-leg first phase, that is, a time point when the heel is grounded on the ground surface and it corresponds to a starting point of the motion pattern. The mid stance point MS is a switching point when the standing-leg first phase is switched to the standing-leg second phase. The heel off point HO is a switching point when the standing-leg second phase is switched to the free-leg first phase, that is, it corresponds to a time point when the toe leaves the ground surface. The swing point SW is a switching point when the free-leg first phase is switched to the free-leg second phase.

Then, regarding a time ratio between the standing-leg cycle and the free-leg cycle in the walking motion cycle T, it is known that the ratio 6:4 is functionally appropriate regardless of the paralytic symptoms of the wearer M or individual differences. Thus, a time point after 0.6 T has elapsed since the heel contact point HC is set to the heel off point HO, and a period of the 0.6 T between them is set as the standing-leg cycle, and a period of the other 0.4 T as the free-leg cycle. Further, regarding the time ratio between the standing-leg first phase and the standing-leg second phase in the standing-leg cycle, it is known that the ratio 1:1 is functionally appropriate. Thus, a time point (a mid time point of the standing-leg cycle) after 0.3 T has elapsed since the heel contact point HC is set to the mid stance point MS, and a time point after 0.3 T has elapsed since this mid stance point MS is set to the heel off point HO. Moreover, regarding the time ratio between the free-leg first phase and the free-leg second phase in the free-leg cycle, it is known that the ratio 1:1 is functionally appropriate. Thus, a time point (a mid time point of the free-leg cycle) after 0.2 T has elapsed since the heel off point HO is set to the swing point SW, and a time point after 0.2 T has elapsed since this swing point SW is set to the heel contact point HC.

As described above, in each of the motion phases time-divided by the four switching points HC, MS, HO, and SW, a motion pattern in which the turning angle of the drive mechanism 11 is monotonically increased or monotonically decreased is set. That is, the turning angle monotonically increases in the standing-leg first phase, monotonically decreases in the standing-leg second phase, monotonically increases in the free-leg first phase, and monotonically decreases in the free-leg second phase. Note that, in this embodiment, the turning motion of the drive mechanism 11 in each motion phase is performed at a linear equal speed. That is, the motor control part 32 of the controller 8 drives the drive motor 9 in each motion phase by equal-speed control. As described above, as indicated by a solid line (control angle) in the illustration of the ankle turning angle, a motion pattern regulating a change in the turning angle of the drive mechanism 11 with time forms a temporal waveform linearly connecting the adjacent switching points HC, MS, HO, and SW to each other. Note that, in this embodiment, the motion pattern is set in compliance with the turning angle (ankle turning angle) of the drive mechanism 11. Thus, in actual driving, the motor control part 32 sequentially converts the corresponding turning angle to a motor rotation angle as appropriate and outputs a motor drive instruction as a position instruction to the amplifier 22.

Moreover, even in the case that the drive motor 9 is actually driven by the amplifier 22 at the equal speed, since acceleration and deceleration are performed at both ends of the equal-speed driving, strictly speaking, the turning angle changes in a curved manner close to a sinusoidal wave in the vicinity of each of the switching points HC, MS, HO, and SW (not particularly shown). In consideration of this point, the motion pattern may be set with a temporal waveform connecting each of the switching points HC, MS, HO, and SW with a substantially curved line. Setting the motion pattern with a temporal waveform which is actually a substantially curved line changes smoothly the turning angle of the drive mechanism 11, and allows corrected driving without giving a sense of discomfort to the wearer M.

Then, the caregiver who is an operator of the controller 8 adjusts and sets the turning angle in each of the four switching points HC, MS, HO, and SW as appropriate in accordance with the paralytic symptoms of the wearer M and the individual differences. At this time, a shape of the temporal waveform (solid-line waveform) of the motion pattern linearly connecting those switching points HC, MS, HO, and SW should be a waveform shape substantially close to a temporal change curve (dotted waveform) of the normal ankle turning angle, that is, a shape having a mountain-shaped waveform in each of the standing-leg cycle and the free-leg cycle. For that purpose, it is desirable that the turning angles are set with limitation so that the turning angle at the heel contact point HC is within a range of 0° to 10°, the turning angle at the mid stance point MS is within a range of 0° to 15°, the turning angle at the heel off point HO is within a range of −10° to 20°, and the turning angle at the swing point SW is within a range of 0° to 25°.

According to the aforementioned method, the caregiver only sets and inputs an arbitrary turning angle limited to the four switching points HC, MS, HO, and SW, and thereby it is possible to set a motion pattern which is sufficiently functional to be used for rehabilitation, and to simplify an operation of input setting by reducing the number of times of adjustment/setting of the turning angle.

Note that an arrow direction at each time point in the illustration in a motor assist direction in FIG. 5 follows a turning direction (dorsal flexion side or plantar flexion side) of the control angle on the motion pattern indicated by the solid line in the illustration of the ankle turning angle. That is, at each time point during the walking motion cycle T, the drive motor 9 and the drive mechanism 11 are forcedly turned in the arrow direction indicated by the illustration of the motor assist direction with respect to the ankle joint of the wearer M. Moreover, during the standing-leg cycle or particularly during a period of the standing-leg first phase, it is known that a rotary torque to be forcedly given by the drive mechanism 11 to the ankle joint of the wearer M, that is, a drive torque of the drive motor 9 is preferably relatively small in consideration of stability of the standing leg. Further, during the free-leg cycle (particularly during a period of the free-leg first phase), since the entire foot is away from the ground surface, it is known that even if the rotary torque of the drive mechanism 11 (the drive torque of the drive motor 9) is made relatively large, it does not influence stability of the walking motion. Thus, as an element of the motion pattern, it is useful to set the drive motor 9 capable of torque control so that the drive torque is made relatively small in the standing-leg first phase, while the drive torque is made relatively large in the free-leg cycle (may be only the free-leg first phase). In the case of performing such torque control, specifically, the motor control part 32 may perform torque limitation or torque addition on a torque instruction to a feedback loop of the amplifier 22 or increasingly/decreasingly modify a position control gain or a speed control gain during the cycle of the corresponding motion phase, although not particularly shown.

Further, the solid curve illustrated in the illustration of the grounding pressure in FIG. 5 illustrates an exemplary temporal change of the grounding pressure of the heel detected by the heel-side pressure-sensitive sensor 7, and a one-dot chain curve illustrates an exemplary temporal change of the grounding pressure of the thenar detected by the toe-side pressure-sensitive sensor 6. As illustrated, the heel grounding pressure rapidly increases at the heel contact point HC, becomes substantially constant only during the standing-leg cycle, and rapidly decreases before the heel off point HO. In this embodiment, the motor control part 32 synchronizes the motion pattern by using the temporal change of this heel grounding pressure. That is, a predetermined threshold value B is set lower than the constant grounding pressure during the standing-leg cycle, the motion pattern is started by using a time point when the detection value of the heel-side pressure-sensitive sensor 7 exceeds the threshold value B as a standing-leg cycle trigger, that is, as the heel contact point HC, and the turning motion of the drive mechanism 11 is controlled in accordance with the motion pattern after that. During execution of this walking motion, the motion pattern may be executed so as to be cyclically repeated after synchronization is once established or may be executed so that the motion pattern is started every time the standing-leg cycle trigger is detected.

5. Selection/Setting of Walking Speed Mode

In this embodiment, a walking speed can be also adjusted by use of the motion pattern set as above. For example, in order to change a moving speed of the wearer M himself/herself, a time length of the entire walking motion cycle T may be changed. However, in addition to above, there is a method of changing a change speed of the ankle turning angle while the walking motion cycle T is maintained. It is known that, by the change of a speed of the swing back motion of the foot mainly during a period from the heel off point HO to the swing point SW, that is, in the free-leg first phase, a step size in the free-leg cycle is changed, whereby the walking speed changes particularly largely. In correspondence with that, as illustrated in FIG. 6 in which the illustration of the ankle turning angle in FIG. 5 is enlarged, a change speed of the ankle turning angle in the free-leg first phase, that is, a linear inclination on the motion pattern can be changed in this embodiment.

Specifically, in the setting processing of the motion pattern, three modes, that is, a normal mode (Normal in the figure), a quick mode (Quick in the figure: large step size), and a slow mode (Slow in the figure: small step size) can be selectively set for a change speed mode of the ankle turning angle in the free-leg first phase (hereinafter, referred to as a "walking speed mode"). However, a time elapse relationship that a cycle length of the free-leg first phase is 0.2 T is fixed. Thus, in the case that the quick mode is set, the change of the ankle turning angle is limited with the set turning angle as an upper limit so as not to exceed the turning angle separately set for the swing point SW which is an end point of the free-leg first phase. In the case that the slow mode is set, a set turning angle at the swing point SW is also changed so as to decrease in accordance with the change speed of the ankle turning angle in the free-leg first phase (SW→SW' in the figure).

6. Specific Operation of Operation Device and Display of Displayer

Subsequently, an exemplary specific operation of the operation device 23 and an exemplary display of the displayer 24 performed in the setting processing of the motion pattern described above will be described. In the setting processing of the motion pattern, for example, as illustrated in an enlarged diagram of the displayer 24 in FIG. 3, each item of the walking motion cycle T ("2.0s" in the illustrated example) is displayed on the left side on an upper stage, the walking speed mode ("Normal" in the illustrated example) at the center on the upper stage, a battery charged state (full-charged state in the illustrated example) on the right side on the upper stage, names of respective switching points of the heel contact point ("HC"), the mid stance point ("MS"), the heel off point ("HO"), and the swing point ("SW") in order from the left side on a medium stage, set turning angles corresponding to the switching points, respectively, from the left side on the lower stage, and "OK?" to confirm setting completion on the right side on the lower stage, respectively.

In the case that any one of the display items described above flashes as an operation target and the two cursor operation keys 43 and 44 are operated, the flashing display is moved on the screen so as to switch the display item, and the operation target can be selected by pressing of the OK key 45. When the cursor operation keys 43 and 44 are further operated, contents of the operation target (the walking motion cycle T, the walking speed mode, the turning angle) are set, and the operation to determine or to stop the setting contents is performed by use of the OK key 45 or the cancellation key 46.

Here, as described above, the motion assisting apparatus 1 is used for rehabilitation of the walking motion of the wearer M who is a paralytic or the like, and during this rehabilitation work, one caregiver (not particularly shown), for example, assists the walking motion while supporting the body of the wearer M from the side. At this time, since the controller 8 including the operation device 23 and the displayer 24 is arranged on the back surface of the waist part of the wearer M as described above, the wearer M cannot operate or visually recognize them but only the caregiver can operate the operation device 23 easily with a hand while visually checking the display contents of the displayer 24. Particularly since the power switch 42 can be used for emergency stop during the walking motion, it is arranged at a position where the wearer M cannot easily operate it but only the caregiver can easily operate it.

7. Control Flow of Motion Pattern Setting Processing

In order to realize the functions as described above, an exemplary control procedure of the motion pattern setting processing executed by the CPU (arithmetic device) included in the microcomputer 21 of the controller 8 in the motion pattern setting part 31 will be described in order with reference to FIG. 7. First, in FIG. 7, execution of the processing illustrated in this flow is started when a motion mode is switched to the mode for setting a motion pattern by an input operation in the operation device 23.

First, at process S105, the CPU of the microcomputer 21 sets a time length of the walking motion cycle T. Here, a specific method of setting this walking motion cycle T may include setting of an arbitrary time length by an operation input by the caregiver or measurement in a separate measurement mode during a walking motion in a state where the wearer M actually wears the motion assisting apparatus 1.

Then, the routine proceeds to process S110, and the CPU of the microcomputer 21 selectively sets a walking speed mode in the free-leg first phase described in FIG. 6.

Then, the routine proceeds to process S115, and the CPU of the microcomputer 21 sets a turning angle at each of the four switching points HC, MS, HO, and SW. Note that the setting operation at process S110 and this process S115 may be performed by the operation described in FIG. 3.

Subsequently, the routine proceeds to process S120, and the CPU of the microcomputer 21 calculates a change speed (linear inclination in the pattern waveform) of the turning angle in each motion phase on the basis of the setting at process S110 and process S115. In the normal case, the change speed of the turning angle may be calculated simply from a cycle length between the switching points and a difference in the turning angle, but in the case that the walking speed mode is set to the quick mode or the slow mode, the change speed of the turning angle in the free-leg first phase or in the free-leg second phase is calculated also in consideration of an upper limit and a change in the turning angle.

Subsequently, the routine proceeds to process S125, and the CPU of the microcomputer 21 sets the entire motion pattern on the basis of the setting and the calculation result at process S105 to process S120. Then, this flow is finished.

8. Effect of this Embodiment

As described above, according to the controller 8 of the motion assisting apparatus 1 of this embodiment, the motion pattern setting part 31 of the microcomputer 21 sets the motion pattern by time-dividing the motion pattern of the turning angle of the drive mechanism 11 during the walking motion cycle by the unit of the motion phase for monotonic increase or monotonic decrease and by setting the turning angle of the drive mechanism 11 at the switching points HC, MS, HO, and SW between those motion phases. As a result, a motion pattern which is sufficiently functional to be used for rehabilitation can be set. Then, the motor control part 32 controls driving of the drive motor 9 on the basis of the motion pattern. As a result, the number of items to be set can be reduced and as a result, setting of the motion pattern of the motion assisting apparatus 1 in accordance with the situation of the wearer M can be simplified, whereby operability can be improved.

Moreover, particularly in this embodiment, the motion pattern setting part 31 sets the motion pattern so that the standing-leg first phase in which the turning angle of the drive mechanism 11 is monotonically changed to the dorsal flexion side in the standing-leg state, the standing-leg second phase in which the turning angle of the drive mechanism 11 is monotonically changed to the plantar flexion side in the standing-leg state, the free-leg first phase in which the turning angle of the drive mechanism 11 is monotonically changed to the dorsal flexion side in the free-leg state, and the free-leg second phase in which the turning angle of the drive mechanism 11 is monotonically changed to the plantar flexion side in the free-leg state are executed in order as the motion phases in one cycle of the walking motion cycle. As a result, the motion phase can be divided simply and functionally to the fewest number of sections (four) in one cycle of the walking motion cycle, and the setting operation of the motion pattern can be simplified. Note that the motion phase may be divided into more motion phases on the basis of an actual turning angle change pattern in the ankle joint of a healthy person. Further, the walking motion can be performed at whatever motion phase the walking motion cycle is started as long as the cyclic execution order of each motion phase is abided by.

Moreover, particularly in this embodiment, the motion pattern setting part 31 sets the heel contact point HC which is the switching point between the free-leg second phase and the standing-leg first phase as the starting point of the walking motion cycle. As a result, the walking motion cycle can be functionally started on the basis of a front grounding motion in the ankle joint on the wearing side.

Moreover, particularly in this embodiment, the motion pattern setting part 31 sets the heel off point HO which is the switching point between the standing-leg second phase and the free-leg first phase to a time point after substantially 0.6 T since the heel contact point HC. As a result, the standing-leg cycle and the free-leg cycle can be divided from each other with a time ratio close to that of a healthy person, and the walking motion can be corrected with a functional motion pattern close to normal.

Moreover, particularly in this embodiment, the motion pattern setting part 31 sets the mid stance point MS which is the switching point between the standing-leg first phase and the standing-leg second phase to a substantially intermediate time point of the period from the heel contact point HC to the subsequent heel off point HO. As a result, the standing-leg first phase and the standing-leg second phase can be divided from each other with a time ratio close to that of a healthy person, and the walking motion can be corrected with a functional motion pattern close to normal.

Moreover, particularly in this embodiment, the motion pattern setting part 31 sets the swing point SW which is the switching point between the free-leg first phase and the free-leg second phase to a substantially intermediate time point of the period from the heel off point HO to the subsequent heel contact point HC. As a result, the free-leg first phase and the free-leg second phase can be divided from each other with a time ratio close to that of a healthy person, and the walking motion can be corrected with a functional motion pattern close to normal.

Moreover, particularly in this embodiment, the motor control part 32 executes drive control of the drive motor 9 on the basis of the motion pattern as the heel contact point HC when the grounding pressure detected by the heel-side pressure-sensitive sensor 7 exceeds the predetermined threshold value B. As a result, it is possible to reliably synchronize the actual walking motion of the wearer M with the motion pattern of the drive mechanism 11 by matching timings of the actual heel contact motion of the wearer M and the heel contact point HC on the motion pattern with each other.

Note that, not limited to the above, the motion control part 32 may execute the drive control of the drive motor 9 on the basis of the motion pattern as the heel off point HO when the grounding pressure detected by the toe-side pressure-sensitive sensor 6 falls below the similar threshold value B. In this case, it is possible to reliably synchronize the actual walking motion of the wearer M with the motion pattern of the drive mechanism 11 by matching timings of the actual heel off motion of the wearer M and the heel off point HO on the motion pattern with each other. As a result, even if the paralytic wearer M is walking without grounding the heel or with grounding in the order from the thenar to the heel, such a case can be handled.

Moreover, particularly in this embodiment, the motor control part 32 drives the drive motor 9 by equal-speed control in each motion phase. As a result, it is possible to realize the drive control of the drive motor 9 with a simple processing configuration without executing positional control such as following a complicated curved waveform.

Moreover, particularly in this embodiment, the motion pattern setting part 31 can arbitrarily select a drive speed of the drive motor 9 in the free-leg first phase regardless of the turning angle of the drive mechanism 11 set at the swing point SW. As a result, a step size in the free-leg cycle can be adjusted, that is, the walking speed can be changed (walking speed mode can be selected) even in the same walking motion cycle T. Here, the step size can be adjusted also by the change of the drive speed of the drive motor 9 in the standing-leg first phase, but in consideration of stability in the walking motion, a change only in the free-leg first phase is desirable.

Moreover, particularly in this embodiment, the motor control part 32 can increasingly/decreasingly modify the drive torque of the drive motor 9 in a predetermined motion phase. As a result, stability in the walking motion and a correcting function of the ankle turning angle are improved.

Moreover, particularly in this embodiment, the controller 8 is accommodated in the same housing 41 together with the operation device 23 capable of the setting operation of the turning angles of the drive mechanism 11 at the switching points HC, MS, HO, and SW and the displayer 24 capable of setting display of the turning angles of the drive mechanism 11 at the switching points HC, MS, HO, and SW and is attached to the body of the wearer M. As a result, even if the caregiver sets the motion pattern while supporting the body of the wearer M, there is no need to take up a separate operation terminal by hand for operation, and operability is improved.

Moreover, particularly in this embodiment, the controller 8 is attached to the back surface of the waist part of the wearer M. As a result, even if the caregiver sets the motion pattern while supporting the body of the wearer M, visual check of the input operation to the operation device 23 or the displayer 24 is facilitated by the arrangement, and operability is improved.

9. Modification

Note that the embodiment of the disclosure is not limited to the above, and is capable of various modifications within a range not departing from the gist and technical idea thereof. Such modifications will be described below.
(Modification 1: Relationship Between Turning Angle and Motor Rotation Angle)

In the embodiment, the rotation sensor 12 detects the rotation angle of the drive motor 9 but this is not limiting. For example, the rotation sensor 12 may detect a relative rotation angle (ankle turning angle) between the shoe part 5 and the shin-part arm 4 and in this case, it is disposed between the decelerator and the drive shaft of the drive mechanism 11 (not shown). In this case, the turning angle of the drive mechanism 11 detected by the rotation sensor 12 is input into the microcomputer 21 through the cable 10, and positional feedback control by a so-called full-closed loop is executed by the motor control part 32 and the amplifier 22.

Note that the motion pattern itself may be also set on the basis of the motor rotation angle. In this case, the ankle turning angles input in the operation device 23 corresponding to the switching points HC, MS, HO, and SW are converted to the motor rotation angles as appropriate, respectively, and a change waveform of the motion pattern is set (not particularly illustrated). In this case, too, the rotation sensor 12 may detect either one of the turning angle of the drive mechanism 11 and the rotation angle of the drive motor 9 and may execute the drive control of the drive motor 9 by converting the turning angle and the rotation angle as appropriate when necessary.
(Modification 2: Individual Synchronization of Standing-Leg Cycle and Free-Leg Cycle)

In the embodiment, one motion pattern across the entire walking motion cycle T is created, and the time ratio between the standing-leg cycle and the free-leg cycle in it is fixed to 6:4, but this is not limiting. In addition, the motion pattern may also be set and generated separately for the standing-leg cycle and the free-leg cycle, and each of the motion patterns may be synchronized and executed at the heel contact point HC and the heel off point HO (not shown). In this case, control of the turning motion of the drive mechanism 11 is started in accordance with a motion pattern of a standing-leg cycle alone with a time point when a detection value of the heel-side pressure-sensitive sensor 7 exceeds the threshold value B, for example, as a standing-leg cycle trigger, that is, as the heel contact point HC. Moreover, control of the turning motion of the drive mechanism 11 is started in accordance with a motion pattern of a free-leg cycle alone with a time point when the detection value of the toe-side pressure-sensitive sensor 6 falls below the threshold value B as a free-leg cycle trigger, that is, as the heel off point HO (actually, a toe off point where the toe leaves the ground surface).

Moreover, depending on the paralytic symptom of the wearer M, only either one of the heel and the toe can be grounded on the ground surface in some cases. In the case that only the heel can be grounded, for example, with a time point when the detection value of the heel-side pressure-sensitive sensor 7 exceeds the threshold value B set to the heel contact point HC as in the embodiment, and synchronization may be established with the one motion pattern across the entire walking motion cycle T only at this single point. Alternatively, with a time point when the detection value of the heel-side pressure-sensitive sensor 7 falls below the threshold value B set to the heel off point HO, and synchronization may be established with the one motion pattern across the entire walking motion cycle T only at this single point. Alternatively, the two points of the heel contact point HC and the heel off point HO are detected only by comparison between the detection value of the heel-side pressure-sensitive sensor 7 and the threshold value B, and the motion pattern of the corresponding standing-leg cycle alone and the motion pattern of the corresponding free-leg cycle alone may be synchronized individually at these two points, respectively.

In the case that only the toe can be grounded, with a time point when the detection value of the toe-side pressure-sensitive sensor 6 exceeds the threshold value B set to the heel contact point HC (actually, a toe contact point where the toe is grounded on the ground surface), and synchronization may be established with the one motion pattern across the entire walking motion cycle T only at this one point as in the embodiment. Alternatively, with a time point when the detection value of the toe-side pressure-sensitive sensor 6 falls below the threshold value B set to the heel off point HO (actually, a toe off point where the toe leaves the ground surface), and synchronization may be established with the one motion pattern across the entire walking motion cycle T only at this one point. Alternatively, the two points of the heel contact point HC and the heel off point HO are detected only by comparison between the detection value of the heel-side pressure-sensitive sensor 7 and the threshold value B, and the motion pattern of the corresponding standing-leg cycle alone and the motion pattern of the corresponding free-leg cycle alone may be synchronized individually at these two points, respectively.

Sorting of the cases into the modification 1 and the modification 2 described above may be enabled to be switched/set arbitrarily by a user through an operation input in the operation device 23.

10. Exemplary Hardware Configuration of Controller

An exemplary hardware configuration will be described for the controller 8 achieving the processes of the motion pattern setting part 31, the motor control part 32, etc. implemented by a program executed by the CPU 901 described above, with reference to FIG. 8.

As shown in FIG. 8, the controller 8 has the circuitry including a CPU 901, a ROM 903, a RAM 905, a dedicated integrated circuit 907 constructed for specific use such as an ASIC or an FPGA, an input device 913, an output device 915, a storage device 917, a drive 919, a connection port 921, and a communication device 923. These constituent elements are mutually connected via a bus 909 and an I/O (input/output) interface 911 such that signals can be transferred.

The program can be recorded in a recording device such as the ROM 903, the RAM 905, and the storage device 917, for example.

The program can also temporarily or permanently be recorded in a removable recording medium 925 such as magnetic disks including flexible disks, various optical disks including CDs, MO disks, and DVDs, and semiconductor memories. The removable recording medium 925 as described above can be provided as so-called packaged software. In this case, the program recorded in the removable recording medium 925 may be read by the drive 919 and recorded in the recording device through the I/O interface 911, the bus 909, etc.

The program may be recorded in, for example, a download site, another computer, or another recording device (not shown). In this case, the program is transferred through a network NW such as a LAN and the Internet and the communication device 923 receives this program. The program received by the communication device 923 may be recorded in the storage device 917 through the I/O interface 911, the bus 909, etc.

The program may be recorded in appropriate externally-connected equipment 927, for example. In this case, the program may be transferred through the appropriate connection port 921 and recorded in the storage device 917 through the I/O interface 911, the bus 909, etc.

The CPU 901 executes various process in accordance with the program recorded in the storage device 917 to implement the processes of the motion pattern setting part 31, the motor control part 32, etc. In this case, the CPU 901 may directly read and execute the program from the storage device 917 or may be execute the program once loaded in the RAM 905. In the case that the CPU 901 receives the program through, for example, the communication device 923, the drive 919, or the connection port 921, the CPU 901 may directly execute the received program without recording in the recording device.

The CPU 901 may execute various processes based on a signal or information input from the input device 913 such as a mouse, a keyboard, and a microphone (not shown) as needed.

The CPU 901 may output a result of execution of the process from the output device 915 such as a display device and a sound output device, for example, and the CPU 901 may transmit this process result through the communication device 923 or the connection port 921 as needed or may record the process result into the storage device 917 or the removable recording medium 925.

It is noted that if terms "vertical," "parallel," "plane," etc. are used in the above description, these terms are not used in the exact meanings thereof. Specifically, these terms "vertical," "parallel," and "plane" allow tolerances and errors in design and manufacturing and have meanings of "approximately vertical," "approximately parallel," and "approximately plane."

It is noted that if terms "same," "equal," "different," etc. in relation to a dimension, a size, a shape and a position of the appearance are used in the above description, these terms are not used in the exact meaning thereof. Specifically, these terms "same," "equal," and "different" allow tolerances and errors in design and manufacturing and have meanings of "approximately the same," "approximately equal," and "approximately different."

However, when a value used as a predefined determination criterion or a delimiting value is described such as the threshold value and a reference value, the terms "same," "equal," "different," etc. used for such a description are different from the above definition and have the exact meanings.

Techniques by the embodiment and each modified example may be appropriately combined and utilized in addition to the examples having already described above. Although exemplification is not performed one by one, the embodiment and each modified example are carried out by various changes being applied thereto without departing from the technical idea of the present disclosure.

What is claimed is:
1. A controller for a motion assisting apparatus for a wearer, comprising:
  circuitry configured to
    set switching points in a change in a turning angle of a drive mechanism driven by a drive motor to assist a turning motion of an ankle joint of a wearer, the drive mechanism comprising a decelerator comprising an input shaft connected with an output shaft of the drive motor, a drive shaft arranged coaxially with the ankle joint, a shoe part configured to receive a foot of the wearer, and a shin-part arm configured to be attached to a shin of the wearer, a rotary driving force of the drive motor being decelerated by the decelerator and outputted to the drive shaft, the shoe part performing a relative turning motion around the drive shaft with respect to the shin-part arm,
    set a motion pattern such that the turning angle monotonically increases or monotonically decreases between the switching points, and wherein the turning angle changes in accordance with time in a walking motion cycle in the motion pattern control the drive motor to change the turning angle according to the motion pattern;

an operation device to set the turning angle at the switching point;

a displayer to display setting of the turning angle at the switching point; and a housing on an upper side of which the operation device and the displayer are arranged and which is configured to be attached to a waist part of the wearer, wherein the displayer displays display contents in an inverse direction when the display contents are seen from the wearer.

2. The controller according to claim 1,
wherein a motion phase is a phase in which the turning angle monotonically increases or monotonically decreases between the switching points.

3. The controller for a motion assisting apparatus according to claim 1,
wherein the housing is attached to a back surface of the waist part of the wearer.

4. The controller according to claim 2,
wherein the circuitry is configured to set the motion pattern having a standing-leg first phase in which the turning angle is monotonically changed to a dorsal flexion side in a standing-leg state, a standing-leg second phase in which the turning angle is monotonically changed to a plantar flexion side in the standing-leg state, a free-leg first phase in which the turning angle is monotonically changed to the dorsal flexion side in a free-leg state, and a free-leg second phase in which the turning angle is monotonically changed to the plantar flexion side in the free-leg state, as the motion phases in one cycle of the walking motion cycle.

5. The controller according to claim 4,
wherein the circuitry is configured to set a heel contact point which is the switching point between the free-leg second phase and the standing-leg first phase to a starting point of the walking motion cycle.

6. The controller according to claim 4,
wherein the motion assisting apparatus comprises a detector to detect a grounding pressure of a heel of the wearer, and
wherein the circuitry is configured to control the drive motor based on the motion pattern using a time point when the grounding pressure detected by the detector exceeds a threshold value as a heel contact point which is the switching point between the free-leg second phase and the standing-leg first phase.

7. The controller for a motion assisting apparatus according to claim 4,
wherein the motion assisting apparatus comprises a detector to detect a grounding pressure of a thenar of the wearer, and
wherein the circuitry is configured to control the drive motor based on the motion pattern using a time point when the grounding pressure detected by the detector falls below a threshold value as a heel off point which is the switching point between the standing-leg second phase and the free-leg first phase.

8. The controller for a motion assisting apparatus according to claim 4,
wherein the circuitry is configured to drive the drive motor by equal-speed control in each of the motion phases.

9. The controller for a motion assisting apparatus according to claim 4,
wherein the circuitry is configured to arbitrarily select a drive speed of the drive motor in the free-leg first phase.

10. The controller for a motion assisting apparatus according to claim 4,
wherein the motion assisting apparatus comprises a detector to detect a grounding pressure of a heel of the wearer, and
wherein the circuitry is configured to
control the drive motor based on the motion pattern of the standing-leg first phase and the motion pattern of the standing-leg second phase when the grounding pressure detected by the detector exceeds a threshold value, and
control the drive motor based on the motion pattern of the free-leg first phase and the motion pattern of the free-leg second phase when the grounding pressure detected by the detector falls below a threshold value.

11. The controller for a motion assisting apparatus according to claim 4,
wherein the motion assisting apparatus comprises a detector to detect a grounding pressure of a thenar of the wearer, and
wherein the circuitry is configured to
control the drive motor based on the motion pattern of the standing-leg first phase and the motion pattern of the standing-leg second phase when the grounding pressure detected by the detector exceeds a threshold value, and
control the drive motor based on the motion pattern of the free-leg first phase and the motion pattern of the free-leg second phase when the grounding pressure detected by the detector falls below a threshold value.

12. The controller for a motion assisting apparatus according to claim 4,
wherein the motion assisting apparatus comprises:
a first detector to detect a grounding pressure of a heel of the wearer; and
a second detector to detect a grounding pressure of a thenar of the wearer, and
wherein the circuitry is configured to
control the drive motor based on the motion pattern of the standing-leg first phase and the motion pattern of the standing-leg second phase when the grounding pressure detected by the first detector exceeds a threshold value; and
control the drive motor based on the motion pattern of the free-leg first phase and the motion pattern of the free-leg second phase when the grounding pressure detected by the second detector falls below a threshold value.

13. The controller for a motion assisting apparatus according to claim 4,
wherein the circuitry is configured to increase or decrease a drive torque of the drive motor in a motion phase.

14. The controller according to claim 5,
wherein the circuitry is configured to set a heel off point which is the switching point between the standing-leg second phase and the free-leg first phase at a time point after approximately 0.6 cycles of the walking motion cycle from the heel contact point.

15. The controller according to claim 14,
wherein the circuitry is configured to set a mid stance point which is the switching point between the standing-leg first phase and the standing-leg second phase at an approximately intermediate time point of a period from the heel contact point to the subsequent heel off point.

16. The controller according to claim 14, wherein the circuitry is configured to set a swing point which is the switching point between the free-leg first phase and the free-leg second phase at an approximately intermediate time point of a period from the heel off point to the subsequent heel contact point.

17. A motion assisting apparatus comprising:
a drive motor;
a drive mechanism being driven by the drive motor to assist a turning motion of an ankle joint of a wearer, the drive mechanism comprising a decelerator comprising an input shaft connected with an output shaft of the drive motor, a drive shaft arranged coaxially with the ankle joint, a shoe part configured to receive a foot of the wearer, and a shin-part arm configured to be attached to a shin of the wearer, a rotary driving force of the drive motor being decelerated by the decelerator and outputted to the drive shaft, the shoe part performing a relative turning motion around the drive shaft with respect to the shin-part arm; and
a controller configured to
set switching points in a change in a turning angle of the drive mechanism,
set a motion pattern such that the turning angle monotonically increases or monotonically decreases between the switching points, and herein the turning angle changes in accordance with time in a walking motion cycle in the motion pattern
control the drive motor to change the turning angle according to the motion pattern,
wherein the controller comprises
an operation device to set the turning angle at the switching point;
a displayer to display setting of the turning angle at the switching point; and
a housing on an upper side of which the operation device and the displayer are arranged and which is configured to be attached to a waist part of the wearer, and
wherein the displayer displays display contents in an inverse direction when the display contents are seen from the wearer.

18. A method for controlling a motion assisting apparatus for a wearer, comprising:
using a controller to set switching points in a change in a turning angle of a drive mechanism driven by a drive motor to assist a turning motion of an ankle joint of a wearer, the drive mechanism comprising a decelerator comprising an input shaft connected with an output shaft of the drive motor, a drive shaft arranged coaxially with the ankle joint, a shoe part configured to receive a foot of the wearer, and a shin-part arm configured to be attached to a shin of the wearer, a rotary driving force of the drive motor being decelerated by the decelerator and outputted to the drive shaft, the shoe part performing a relative turning motion around the drive shaft with respect to the shin-part arm;
setting a motion pattern such that the turning angle monotonically increases or monotonically decreases between the switching points using the controller; and wherein the turning angle changes in accordance with time in a walking motion cycle in the motion pattern
controlling the drive motor to change the turning angle according to the motion pattern using the controller,
wherein the controller comprises
an operation device to set the turning angle at the switching point;
a displayer to display setting of the turning angle at the switching point; and
a housing on an upper side of which the operation device and the displayer are arranged and which is configured to be attached to a waist part of the wearer, and
wherein the displayer displays display contents in an inverse direction when the display contents are seen from the wearer.

19. A non-transitory computer-readable recording medium having program code stored thereon which, when executed by a computer, causes a computer to perform a method for controlling a motion assisting apparatus for a wearer, the method comprising:
setting switching points in a change in a turning angle of a drive mechanism driven by a drive motor to assist a turning motion of an ankle joint of a wearer, the drive mechanism comprising a decelerator comprising an input shaft connected with an output shaft of the drive motor, a drive shaft arranged coaxially with the ankle joint, a shoe part configured to receive a foot of the wearer, and a shin-part arm configured to be attached to a shin of the wearer, a rotary driving force of the drive motor being decelerated by the decelerator and outputted to the drive shaft, the shoe part performing a relative turning motion around the drive shaft with respect to the shin-part arm;
setting a motion pattern such that the turning angle monotonically increases or monotonically decreases between the switching points; and wherein the turning angle changes in accordance with time in a walking motion cycle in the motion pattern
controlling the drive motor to change the turning angle according to the motion pattern,
wherein the computer comprises
an operation device to set the turning angle at the switching point;
a displayer to display setting of the turning angle at the switching point; and
a housing on an upper side of which the operation device and the displayer are arranged and which is configured to be attached to a waist part of the wearer, and
wherein the displayer displays display contents in an inverse direction when the display contents are seen from the wearer.

* * * * *